United States Patent [19]
Agblevor

[11] Patent Number: 5,807,952
[45] Date of Patent: Sep. 15, 1998

[54] PROCESS FOR PRODUCING PHENOLIC COMPOUNDS FROM LIGNINS

[75] Inventor: Foster A. Agblevor, Lakewood, Colo.

[73] Assignee: Midwest Research Institute, Kansas City, Mo.

[21] Appl. No.: 641,946

[22] Filed: May 2, 1996

Related U.S. Application Data

[63] Continuation-in-part of Ser. No. 307,439, Sep. 19, 1994, abandoned.

[51] Int. Cl.$^6$ .................... C08H 5/02; C07G 1/00
[52] U.S. Cl. .......................... 527/400; 530/500
[58] Field of Search ............... 527/400; 530/500

[56] References Cited

U.S. PATENT DOCUMENTS

| | | | |
|---|---|---|---|
| 2,221,778 | 11/1940 | Collings et al. | 527/400 |
| 2,227,219 | 12/1940 | Fiedler | 527/400 |
| 2,683,706 | 7/1954 | Muller | 527/400 |
| 3,395,033 | 7/1968 | Remer | 527/400 |
| 4,168,252 | 9/1979 | Makino | 527/100 |
| 4,357,454 | 11/1982 | Holmberg et al. | 527/403 |

FOREIGN PATENT DOCUMENTS 351785  2/1973  U.S.S.R. .

OTHER PUBLICATIONS

Goheen, David W., "Hydrogenation of Lignin by the Noguchi Process," *Lignin Structures and Reactions*, pp. 205–224, 150th Meeting of the American Chemical Society, Atlantic City, NJ, Sep. 13–14, 1965.

Bolkova et al. "Production of Carbons from Pressed Lignin," Poluch; Strukt. Svoistva Sorbentov (1971), 1, 22–6.

Zakis et al. Oxidation of Lignin amd Model Phenols by an Ammonia Solution of Hexacyanoferrate (III), Khim Drew. (1983)2, 56–9.

Hosoya, , Shoji. "Gasification of Lignin," Baliomasu Henkan Keikaku Kenyn Hokoku (1990), 23, 32–45.

*Primary Examiner*—Nathan M. Nutter
*Attorney, Agent, or Firm*—Edna M. O'Connor; Ken Richardson

[57] ABSTRACT

A process for the production of low molecular weight phenolic compounds from lignins through the pyrolysis of the lignins in the presence of a strong base. In a preferred embodiment, potassium hydroxide is present in an amount of from about 0.1% to about 5% by weight, the pyrolysis temperature is from about 400° C. to about 600° C. at atmospheric pressure, and the time period for substantial completion of the reaction is from about 1–3 minutes. Examples of low molecular weight phenolic compounds produced include methoxyphenols, non-methoxylated phenols, and mixtures thereof.

29 Claims, 9 Drawing Sheets

PROCESS FOR PRODUCING PHENOLIC COMPOUNDS FROM LIGNINS

This application is a continuation-in-part application of U.S. patent application Ser. No. 08/307,439, filed Sep. 19, 1994 and now abandoned.

The United States Government has rights in this invention under Contract No. DE AC36-83CH10093 between the United States Department of Energy and the National Renewable Energy Laboratory, a division of the Midwest Research Institute.

BACKGROUND OF THE INVENTION

I. Field of the Invention

The present invention relates to a process for the production of low molecular weight phenolic compounds from lignins through the pyrolysis of the lignins in the presence of a strong base.

II. Description of the Prior Art

Low molecular weight phenolic compounds have great value as precursor products for the production of resins, surfactants, specialty chemicals of various types, anthraquinones for sulfur-free pulping processes, and other applications. Researchers have known that such phenolic compounds, substantially in the form of a liquid as well as other valuable resources, can be produced from lignins, but, at the present time, the employment of lignins as a source material has not been practical since the treatment processes required are costly, complicated and not sufficiently productive. Hydrolysis, hydrogenolysis, pyrolysis and graft copolymerization all have been attempted. Hydrocracking of lignins does produce a reasonable yield of monophenols, but the hydrocracking process requires very high temperatures and very high pressures. Other prior art processes for the degradation of lignins suffer similar disadvantages. For example, a Japanese article entitled; Hosoya, S.; *Gasification of Lignin;* Baiomasu, Henkan, Keikaku, Kenkyu, Hokoku; pp 23, 32–41(1990), teaches a continuous gasification process employed with a pyrolysis reactor. Cellulose, lignin, paper, and other wood products are subjected to continuous gasification. However, a shortcoming of this gasification process is that it uses high temperatures and long resident times, with respect to the present invention, and is run to primarily produce carbon, carbon monoxide and hydrocarbons gases, rather than to produce and/or recover low molecular weight phenolic compounds substantially in liquid form. A In another example, a Russian article entitled Zakis, N. G., et. al; *Oxidation Of Lignin and Model Phenols by an Ammonia Solution of Hexacyanoferrate* (III); Khimiya Drevesiny (2); pp 56–59(1983), employs potassium ferricyanide in an oxidation process with alkali lignin. A drawback of this process is that it is normally used to form an insoluble polymeric amorphous substance, as opposed to forming low molecular weight liquid phenol compounds. In Soviet Union Patent No. 351,785, *A Sorbent From Lignin Preparation by Pyrolysis of Lignin in Presence of Dimethylphosphite;* lignin is pyrolysed in the presence of potassium hydroxide and dimethyl phosphitepxode. A drawback with this pyrolysis process is that it is typically run to make a sorbent with ion-exchange properties, and not to make low molecular weight phenolic compounds.

In another Russian article entitled Boikova, G. I., et. al.; *Production of Carbons From Pressed Lignin;* Poluchenie, Struktura i Svoistva Sorbentov (1); pp 1, 22–26 (1971), cellulose, lignin, paper, and other wood products are dissolved in potassium hydroxide, subjected to compression, and pyrolyzed. A shortcoming of this pyrolysis process is that it employs high temperatures, relative to the present invention, and is normally run to produce a generally solid activated carbon, instead of desired low molecular weight liquid phenolic compound. Therefore, lignins recovered from pulp, paper and biomass conversion industries substantially are going to waste even though these industries can provide a significant amount of lignin by-product. Further, especially in the biomass conversion process employed to produce ethanol for fuel for vehicles, the recovery of valuable resources such as low low molecular weight liquid phenolic compounds from the lignin now being discarded could reduce the ultimate cost of the ethanol since the monetary return on the entire process would be enhanced.

It is therefore apparent that a need exists for producing valuable, low molecular weight phenolic compounds from lignins. Therefore a primary object of the present invention to provide a process for producing such phenolic compounds from lignins wherein the process is accomplished through pyrolysis of the lignins in the presence of a yield-enhancing agent which promotes the production of the phenolic compounds.

Another object of the present invention is to provide a process for producing low molecular weight phenolic compounds through pyrolysis of the lignins wherein the yield-enhancing agent is a strong base, either alone or in combination with another yield-enhancing agent.

Yet another object of the present invention is to provide a process for the production of low molecular weight phenolic compounds from lignins derived from pulp, paper and biomass industries.

These and other objects of the present invention will become apparent throughout the description of the invention which now follows.

SUMMARY OF THE INVENTION

The present invention is a process for the production of a phenolic compound having a molecular weight from about 100 to less than 168 to about 300 Daltons from a single lignin or from a mixture of different lignins. The process, which can be accomplished at atmospheric pressure, comprises pyrolyzing the lignin or mixture of lignins in the presence of from about 0.1% to about 5% by weight of a strong base such as potassium hydroxide, for example, either alone or in combination with from about 0.1% to about 0.9% by weight potassium ferricyanide, at a temperature of from about 400° C. to about 600° C. for a time period sufficient to yield the desired low molecular weight phenolic compound. A sufficient period of time for the reaction to reach substantial completion generally is less than about five minutes. Produced phenolic compounds can be, for example, methoxyphenols, non-methoxylated phenols, and mixtures thereof. Non-limiting examples of the lignin employed in the process can include mixed hardwood organosolv lignin, steam exploded yellow poplar lignin, steam exploded aspen lignin, kraft lignin, bagasse lignin, fungi treated corn stover, and mixtures thereof.

One source of crude lignins is SSF (simultaneous saccharification and fermentation) residue produced during the production of ethanol from biomass using the SSF methodology as known in the art. Because inorganic salts are used in the pretreatment of SSF feedstocks, however, a significant amount of strong base added to the SSF residue reacts first with these inorganic salts and not with the lignins. Consequently, excess base must be employed in order to reach the reaction stage for lignin conversion. It has been found that washing the SSF residue with water to prior treatment with base can reduce the amount of base required for lignin conversion.

When potassium ferricyanide is included, it evolves higher molecular weight material which is broken down by the strong base to a lower molecular weight. The addition of hydrated aluminum hydroxide during the treatment process described herein reduces foaming without affecting product yield or quality.

A by-product produced by the inventive process here described is char. Addition of potassium ferricyanide, as recited above, appears to increase the volatility of the lignin and thereby reduce the amount of char produced. One benefit of such char production is that the char can be further processed to produce high-value carbon molecular sieves which are used in air separations, hydrocarbon separations, chromatography and other pressure-swing adsorption processes. Thus, the present invention provides a significant contribution in the utilization of lignins which otherwise would be little more than a waste product requiring disposal.

DETAILED DESCRIPTION OF THE PREFERRED EMBODIMENT

Figure 1A:
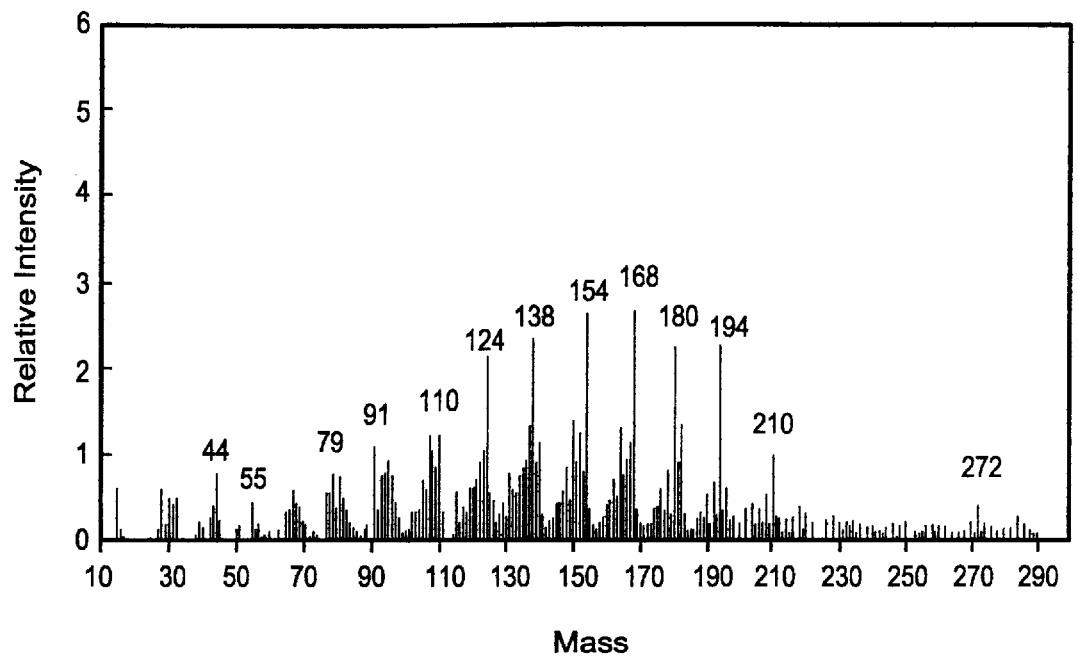
FIGS. 1(a) through 1(d) are graphs showing comparative pyrolysis mass spectra data of lignin.

The preferred embodiment of the present invention is a process for the production of low molecular weight phenolic compounds from lignins through the pyrolysis of the lignins in the presence of potassium hydroxide. The process is described in the Examples that follow.

The preferred embodiment of the present intention is a process for the production of low molecular weight phenolic compounds from lignins through the pyrolysis of the lignins in the presence of potassium hydroxide. Molecular weight is described in *Hawley's Condensed Chemical Dictionary* 12th ed., revised by Richard J. Lewis, Sr.( 1993), as being the sum of the atomic weight of the atoms in a molecule. Atomic weight is further defined in the same source as being the average weight of mass or all isotopes of an element as determined from the proportions on which they are present in a given element compared with the mass of the 12 isotope of carbon (taken as precisely 12 thousand) which is the official international standard.

Mass spectral data acquired from the pyrolysis process in the following examples were analyzed by multivariate statistical techniques. The data were first normalized to the total ion current to account for the sample size variation. Data reduction and resolution were carried out on the normalized data. The correlation around the origin matrix was used in these computations following the method set forth by Windig et. al., in the publication entitled, *Determination of Fractional Concentration and Exact Component Spectra by Factor Analysis of Pyrolysis Mass Spectra of Mixtures,* Chemometrics and Intelligent Laboratory Systems(1987). The factor- data were also presented in polar plots depicting relationship between chemical composition and molecular-beam mass spectrometer pyrolysis data. The factor-analyzed data were resolved into four components corresponding to low-molecular weight dimethoxy phenols, low-molecular weight monomethoxy phenols, low-molecular weight non-methoxylated phenols, and high-molecular weight phenolic compounds. Recovery of relative yields of low molecular weight phenolic compounds substantially in liquid form were estimated from these analysis.

The data indicated that 15%–60% of the lignin subject to the pyrolysis process in accordance with the instant invention were converted into low molecular weight phenolics. The exact yield of low molecular weight phenolic depend on the source of lignin. The process of the instant invention is described in the Examples that follow.

EXAMPLE I(a)

A sample of organosolv lignin was placed into a single stage quench reactor. The reactor was heated to 600° C. at atmospheric pressure for 1–3 minutes, and the vapors produced therefrom were analyzed in real time using a triple quadrupole mass spectrometer as known in the art.

EXAMPLE I(b)

In the same manner as in Example I(a), a second identical sample of organosolv lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

Figure 1B:
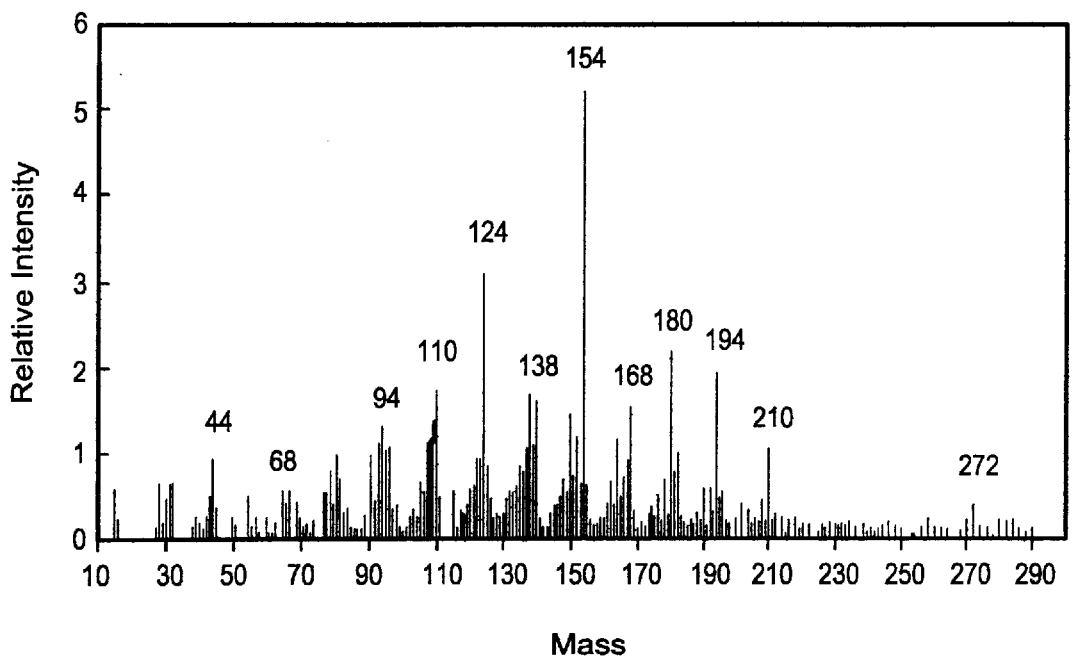
Figure 1C:
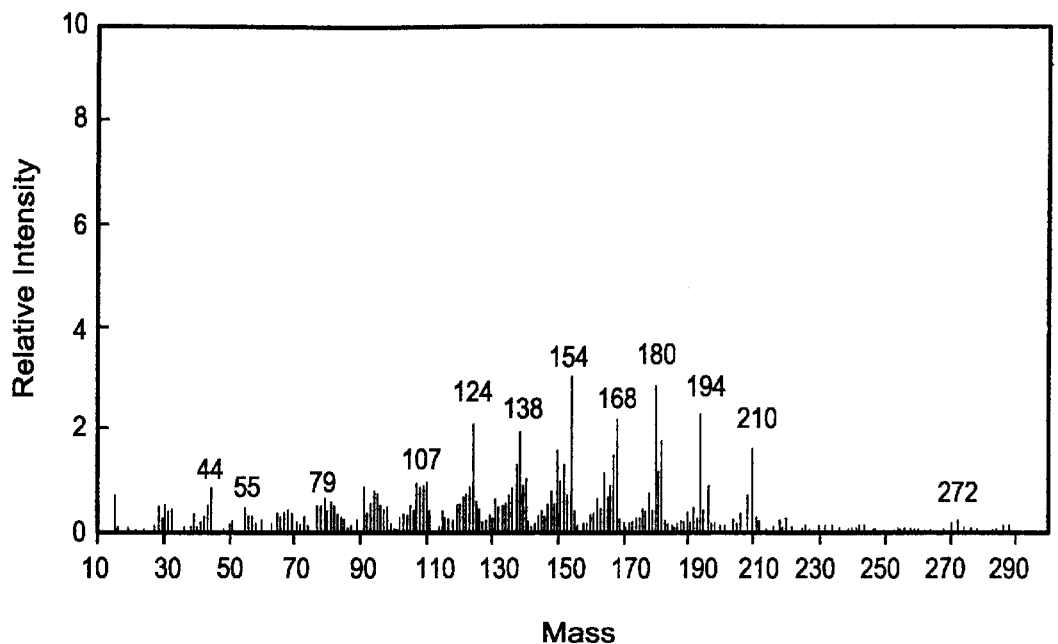
Figure 1D:
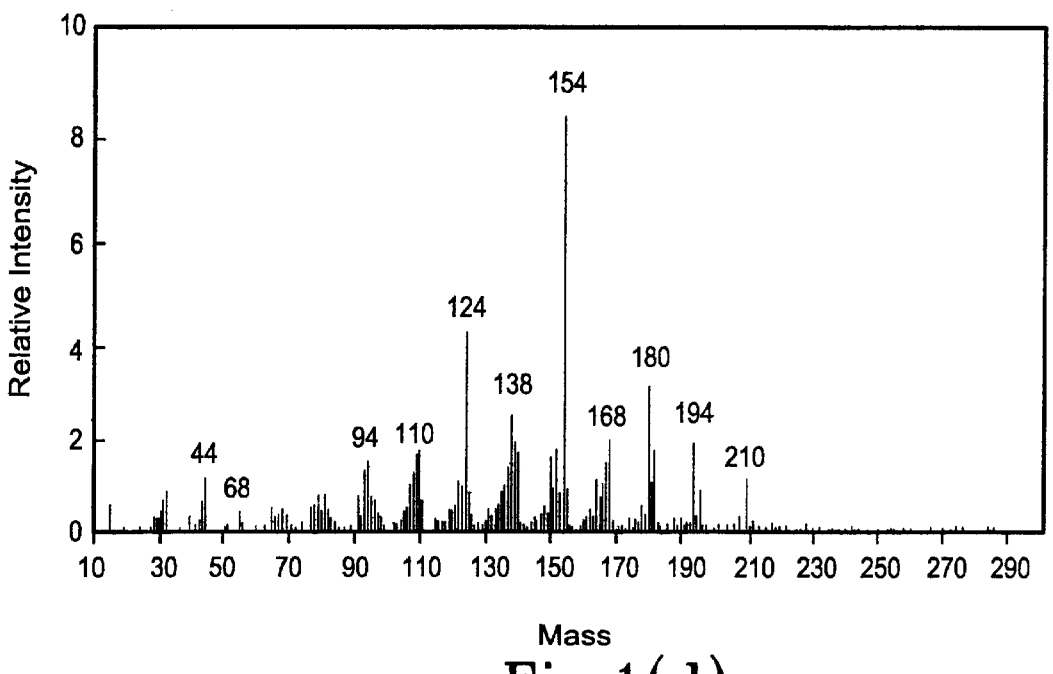

FIGS. 1(a) and 1(b) demonstrate that the primary effect of potassium hydroxide on products obtained from lignin pyrolysis is to promote a narrower slate of low molecular weight phenolic compounds. FIG. 1(a) reflects the results of Example I(a), and FIG. 1(b) reflects the results of Example I(b). As is seen in comparing FIGS. 1(a) and 2(b), the relative intensities of high molecular weight lignin decomposition peaks in FIG. 1(a) for lignin without potassium hydroxide decrease dramatically when potassium hydroxide is present, while the relative intensities of low molecular weight products increase dramatically with potassium hydroxide inclusion.

EXAMPLE II(a)

In the same manner as in Example I(a), a sample of steam exploded aspen lignin was placed in a single stage quench reactor. The reactor was heated to 600° C. at atmospheric pressure for 1–3 minutes, and the vapors produced therefrom were analyzed using the mass spectrometer.

EXAMPLE II(b)

In the same manner as in Example 1(b), a sample of steam exploded aspen lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

FIGS. 2(a) and 2(b) also demonstrate the primary effect of potassium hydroxide on products obtained from lignin pyrolysis. FIG. 2(a) reflects the results of Example II(a), and FIG. 2(b) reflects the results of Example II(b). Once again, the relative intensities of high molecular weight lignin decomposition peaks in FIG. 2(a) for lignin without potassium hydroxide decrease dramatically when potassium hydroxide is present, while the relative intensities of low molecular weight products increase dramatically with potassium hydroxide inclusion.

FIGS. 1 (c) and 1(d) also demonstrate the primary effect of potassium hydroxide on products obtained from lignin pyrolysis. FIG. 1 (c) reflects the results of example II (a), and FIG. 1 (d) reflects the results of Example 11 (b). Once again, the relative intensities of high molecular weight lignin decomposition peaks in FIG. 1 (c) or lignin without potassium hydroxide decrease dramatically when potassium hydroxide is present, while the relative intensities of low molecular weight products increase dramatically with potassium hydroxide inclusion.

Specifically, in all of Examples I(a), I(b), II(a) and II(b), the m/z values shown in the corresponding Figures correspond to a) low molecular weight methoxyphenols (e.g. m/z=124, 139, 150, 154, etc.); b) low molecular weight non-methoxylated phenols and methyl benzenes (e.g. m/z= 92, 94, 106, 108, 122, 136); and c) high molecular weight phenolic compounds (e.g. m/z=168, 180, 194. etc.). Production of the low molecular weight phenolic compounds is thus confirmed when the lignins are pyrolyzed in the presence of potassium hydroxide.

Figure 2:
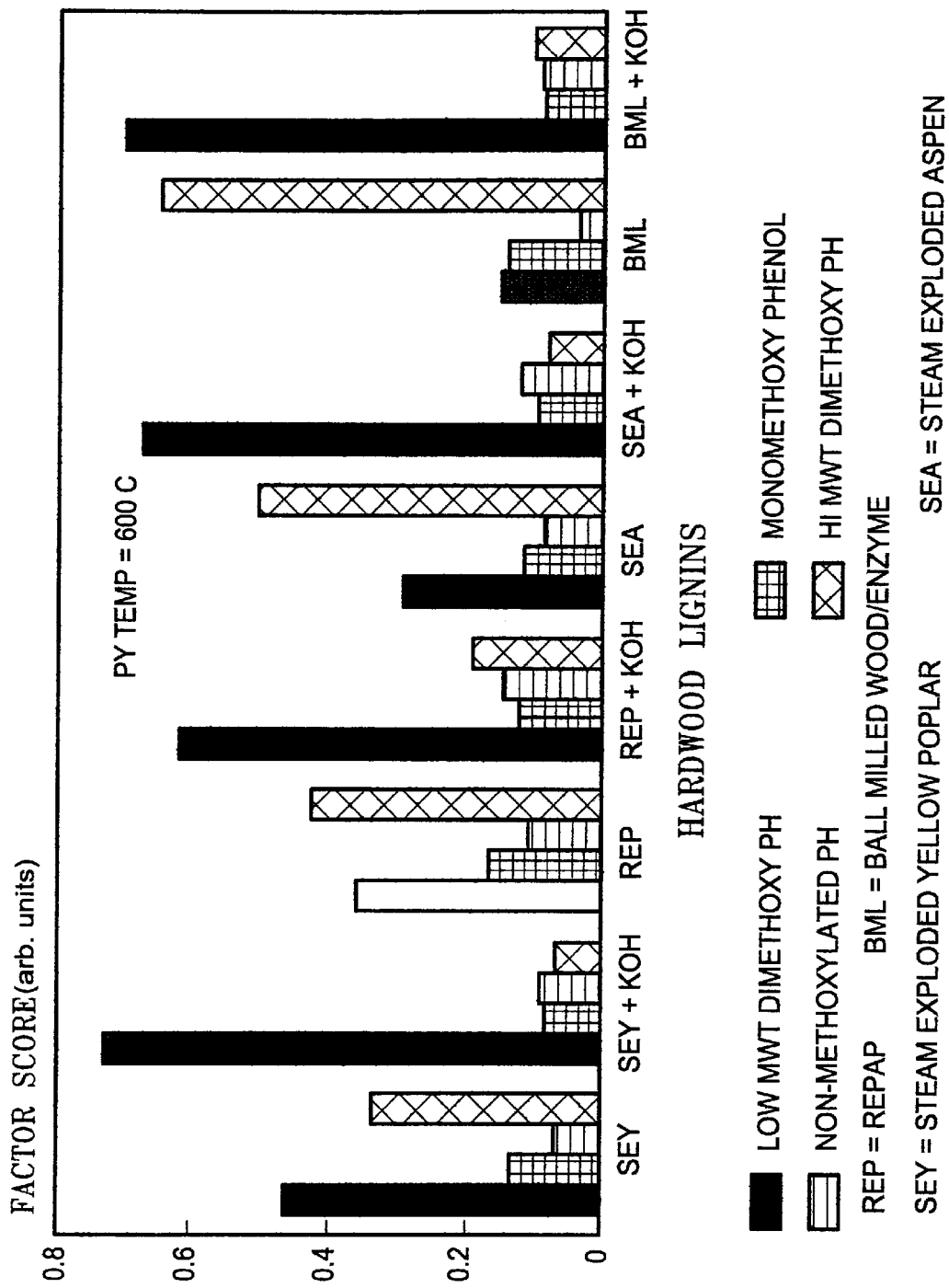
FIG. 2 is a graph showing comparative pyrolysis data of four lignins.

FIG. 2 illustrates the results obtained in Examples III through VI, described as follows.

EXAMPLE III(a)

In the same manner as in Example I(a), a sample of steam exploded yellow poplar (SEP) lignin was placed into a single stage quench reactor. The reactor was heated to 600° C. at atmospheric pressure for 1–3 minutes, and the vapors produced therefrom were analyzed using the mass spectrometer.

EXAMPLE III(b)

In the same manner as in Example I(b), a second identical sample of SEP lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

EXAMPLE IV(a)

In the same manner as in Example I(a), a sample of repap (REP) lignin was placed into a single stage quench reactor. The reactor was heated to 600° C. at atmospheric pressure for 1–3 minutes, and the vapors produced therefrom were analyzed using the mass spectrometer.

EXAMPLE IV(b)

In the same manner as in Example I(b), a second identical sample of REP lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

EXAMPLE V(a)

In the same manner as in Example I(a), a sample of steam exploded aspen (SEA) lignin was placed into a single stage quench reactor. The reactor was heated to 600° C. at atmospheric pressure for 1–3 minutes, and the vapors produced therefrom were analyzed using the mass spectrometer.

EXAMPLE V(b)

In the same manner as in Example I(b), a second identical sample of SEA lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

EXAMPLE VI(a)

In the same manner as in Example I(a), a sample of ball milled wood/enzyme (BML) lignin was placed into a single stage quench reactor. The reactor was heated to 600° C. at atmospheric pressure for 1–3 minutes, and the vapors produced therefrom were analyzed using the mass spectrometer.

EXAMPLE VI(b)

In the same manner as in Example I(b), a second identical sample of BML lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

As is evident in FIG. 2, in all of Examples III through VI, the presence of potassium hydroxide increased the yield of low molecular weight monomethoxy, dimethoxy and non-methoxylated phenols while simultaneously causing a decrease in the production of high molecular weight dimethoxy phenols.

Figure 3:
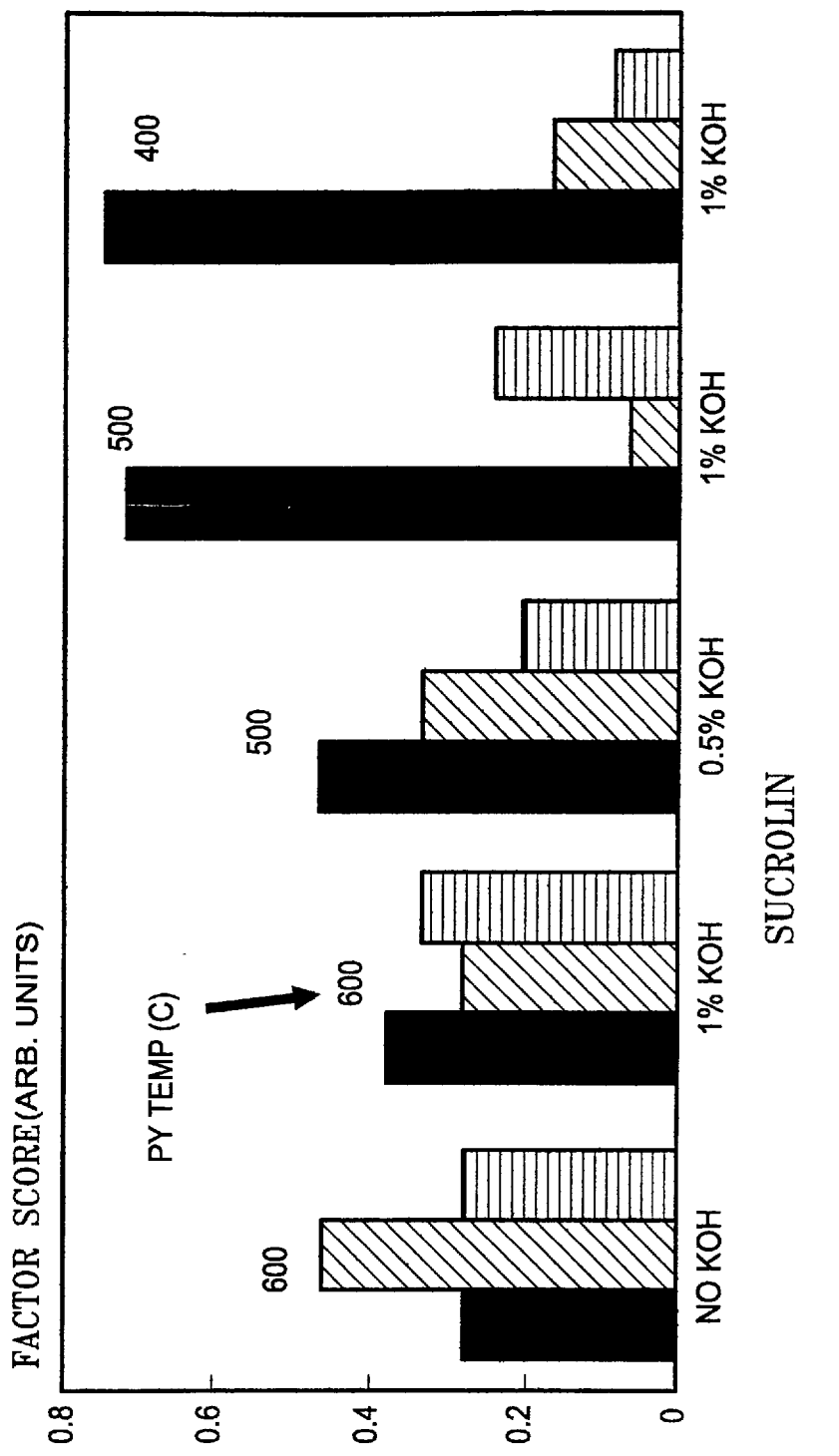
FIG. 3 is a graph showing comparative pyrolysis data of one lignin subjected to selected pyrolyzing conditions.

FIG. 3 illustrates the effects experienced by varying both potassium hydroxide quantity and pyrolysis temperature, as described in Examples VII(a) through VII(e) which follow.

EXAMPLE VII(a)

In the same manner as in Example I(a), a sample of sucrolin (sugar cane bagasse) lignin was placed into a single stage quench reactor. The reactor was heated to 600° C. at atmospheric pressure for 1–3 minutes, and the vapors produced therefrom were analyzed using the mass spectrometer.

EXAMPLE VII(b)

In the same manner as in Example I(b), a second identical sample of sucrolin lignin was placed into a single stage quench reactor along with 1% by weight potassium hydroxide. The reactor was heated to 600° C. at atmospheric pressure for 1–3 minutes, and the vapors produced therefrom were analyzed using the mass spectrometer.

EXAMPLE VII(c)

In the same manner as in Example VII(b), a third identical sample of sucrolin lignin was placed into a single stage quench reactor along with 0.5% by weight potassium hydroxide. The reactor was heated to 500° C. at atmospheric pressure for 1–3 minutes, and the vapors produced therefrom were analyzed using the mass spectrometer.

EXAMPLE VII(d)

In the same manner as in Example VII(b), a fourth identical sample of sucrolin lignin was placed into a single stage quench reactor along with 1% by weight potassium hydroxide. The reactor was heated to 500° C. at atmospheric pressure for 1–3 minutes, and the vapors produced therefrom were analyzed using the mass spectrometer.

EXAMPLE VII(e)

In the same manner as in Example VII(b), a fifth identical sample of sucrolin lignin was placed into a single stage quench reactor along with 1% by weight potassium hydroxide. The reactor was heated to 400° C. at atmospheric pressure for 1–3 minutes, and the vapors produced therefrom were analyzed using the mass spectrometer.

In all of Examples VII(a) through VII(e), measurements were specific to low molecular weight methoxyphenols, non-methoxylated phenols and high molecular weight phenolic compounds. As seen in FIG. 3, the presence of potassium hydroxide at either 0.5% or 1% reduced the amount of high molecular weight compounds produced, with the concentration of potassium hydroxide having a less pronounced effect on low molecular weight yields than did the temperature change.

EXAMPLE VIII(a)

Figure 4A:
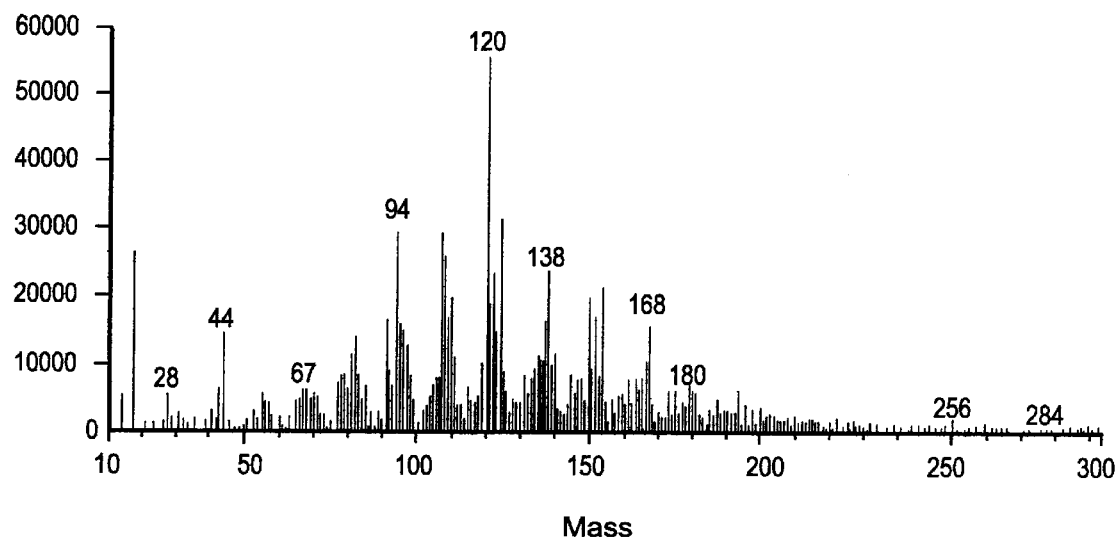
FIGS. 4(a) and (b) are graphs showing comparative pyrolysis data of one lignin using 0.25% potassium hydroxide.

In the same manner as in Example I(a), a sample of sucrolin (sugar cane bagasse) lignin was placed in a single stage quench reactor. The reactor was heated to 600° C. at atmospheric pressure for 1–3 minutes, and the vapors produced therefrom were analyzed using the mass spectrometer as shown in FIG. 4(a).

EXAMPLE VIII(b)

Figure 4B:
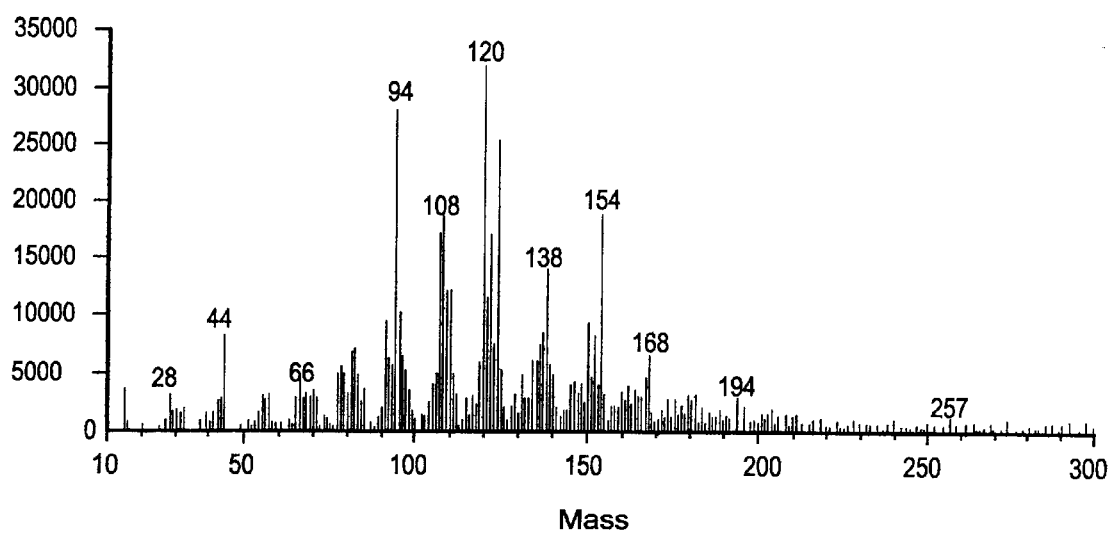

In the same manner as in Example I(b), a second identical sample of sucrolin (sugar cane bagasse) lignin was placed into a single stage quench reactor along with 0.25% by weight potassium hydroxide. The reactor was heated to 600° C. at atmospheric pressure for 1–3 minutes, and the vapors produced therefrom were analyzed using the mass spectrometer. FIG. 4(b) illustrates the overall increased yield of low molecular weight compounds.

EXAMPLE IX(a)

Figure 5A:
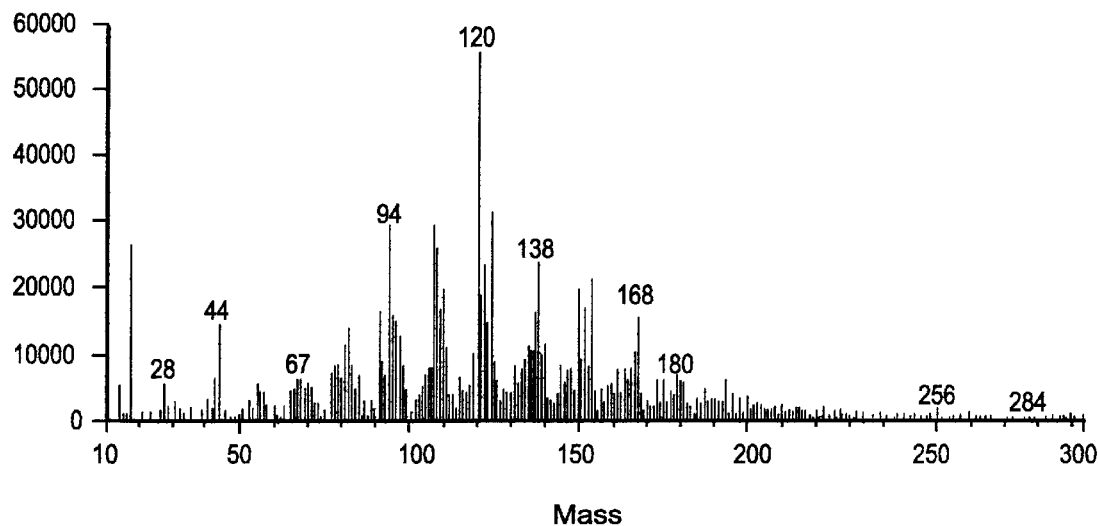
FIGS. 5(a) and (b) are graphs showing comparative pyrolysis data of one lignin using 3% potassium hydroxide.

In the same manner as in Example I(a), a sample of sucrolin (sugar cane bagasse) lignin was placed in a single stage quench reactor. The reactor was heated to 600° C. at atmospheric pressure for 1–3 minutes, and the vapors produced therefrom were analyzed using the mass spectrometer as shown in FIG. 5(a).

EXAMPLE IX (b)

Figure 5B:
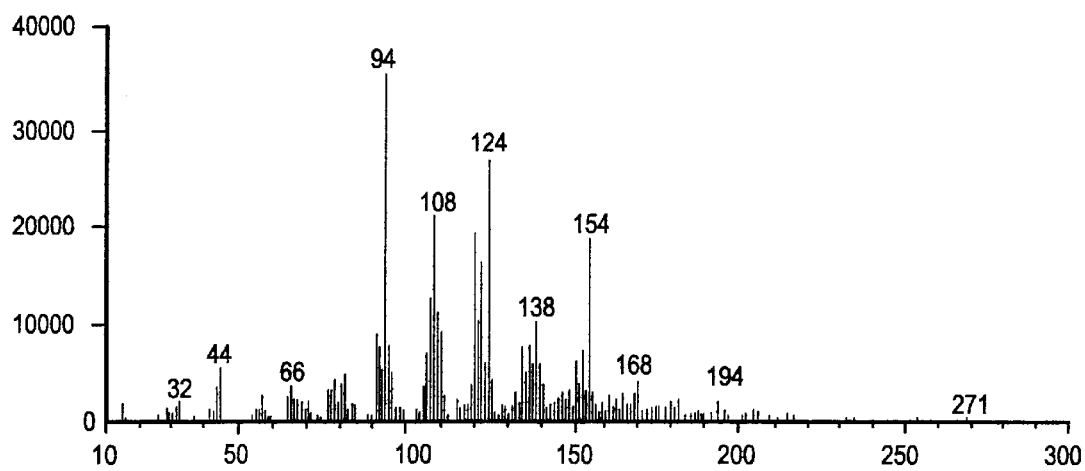

In the same manner as in Example I(b), a second identical sample of sucrolin (sugar cane bagasse) lignin was placed into a single stage quench reactor along with 3% by weight potassium hydroxide. The reactor was heated to 600° C. at atmospheric pressure for 1–3 minutes, and the vapors produced therefrom were analyzed using the mass spectrometer. FIG. 5(b) illustrates the overall increased yield of low molecular weight compounds.

Pyrolysis of the sucrolin converted 50%–60% of the sucrolin into low molecular weight phenolics. The char produced varied from 30%–50 percent (wt) of the lignin.

EXAMPLE X(a)

Figure 6A:
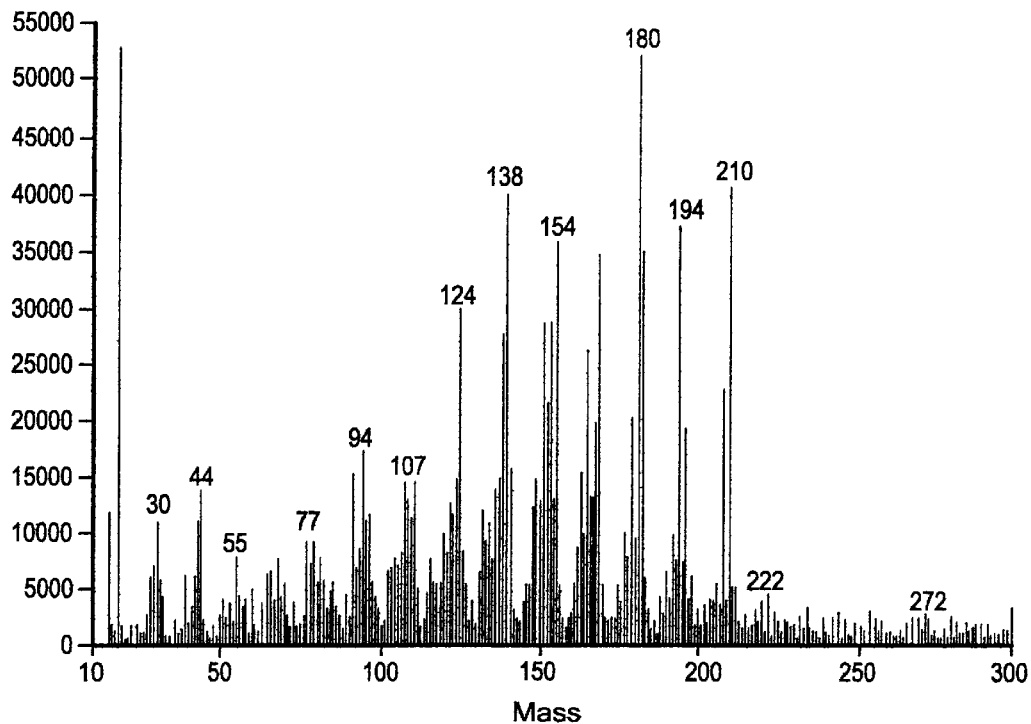
FIGS. 6(a) and (b) are graphs showing comparative pyrolysis data of one lignin using potassium hydroxide and potassium ferricyanide.

In the same manner as in Example I(a), a sample of ball milled wood lignin was placed in a single stage quench reactor. The reactor was heated to 600° C. at atmospheric pressure for 1–3 minutes, and the vapors produced therefrom were analyzed using the mass spectrometer as shown in FIG. 6(a).

EXAMPLE X(b)

Figure 6B:
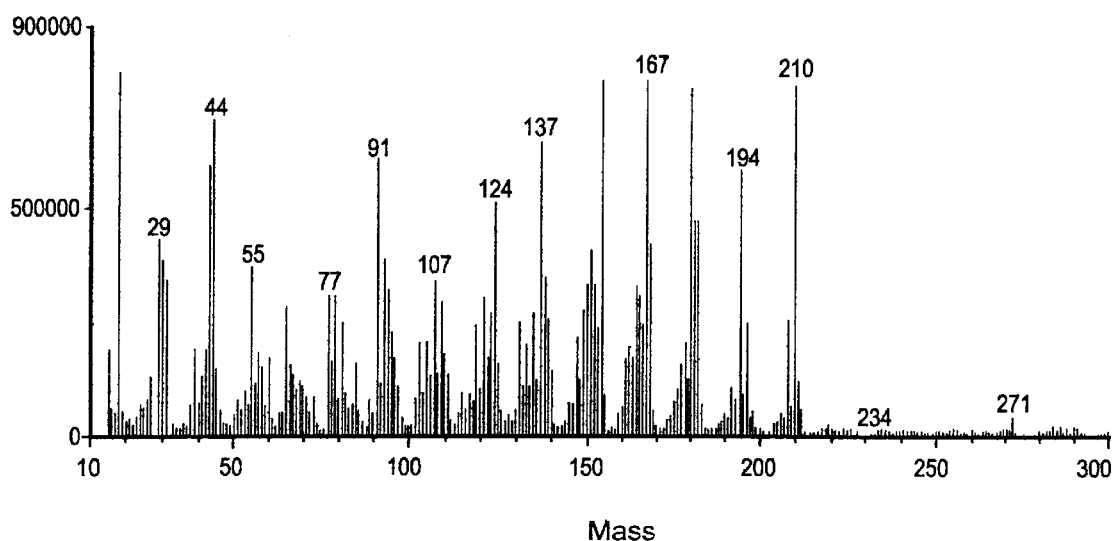

In the same manner as in Example I(b), a second identical sample of ball milled wood lignin was placed into a single stage quench reactor along with 2.5% by weight potassium hydroxide and 2% by weight potassium ferricyanide. The reactor was heated to 600° C. at atmospheric pressure for 1–3 minutes, and the vapors produced therefrom were analyzed using the mass spectrometer. FIG. 6(b) illustrates the increased molecular-weight intensity at, for example, 210, 194, 91 and 44.

EXAMPLE XI(a)

Figure 7A:
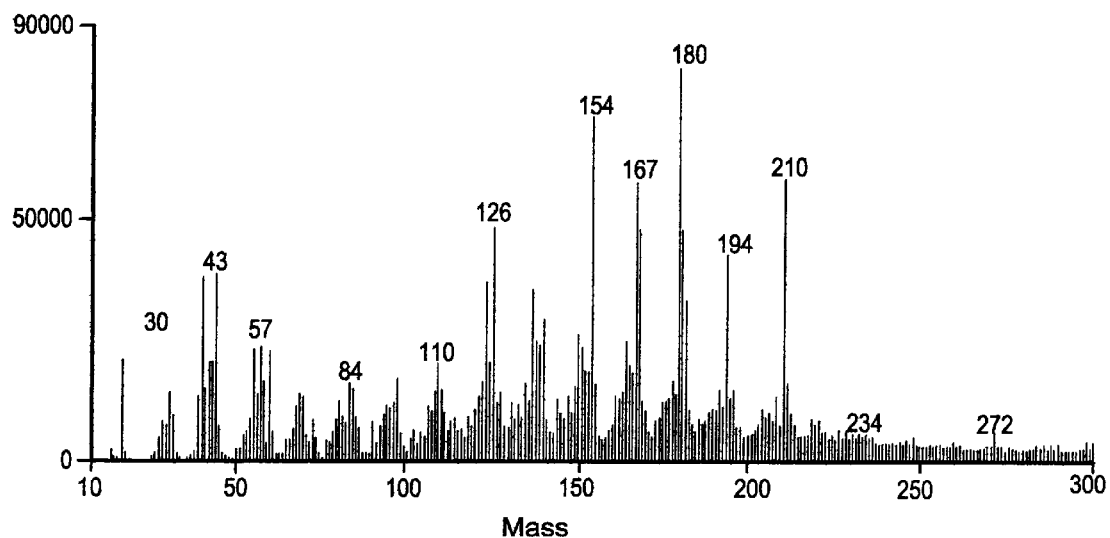
FIGS. 7(a) and (b) are graphs showing comparative pyrolysis data of a first crude lignin whose source is an SSF (simultaneous saccharification and fermentation) residue.

In the same manner as in Example I(a), a sample of simultaneous saccharification and fermentation (SSF) residue (crude lignin) from ethanol production was placed in a single stage quench reactor. The crude lignin residue was from American sycamore wood. The reactor was heated to 600° C. at atmospheric pressure for 1–3 minutes, and the vapors produced therefrom were analyzed using the mass spectrometer as shown in FIG. 7(a).

EXAMPLE XI(b)

Figure 7B:
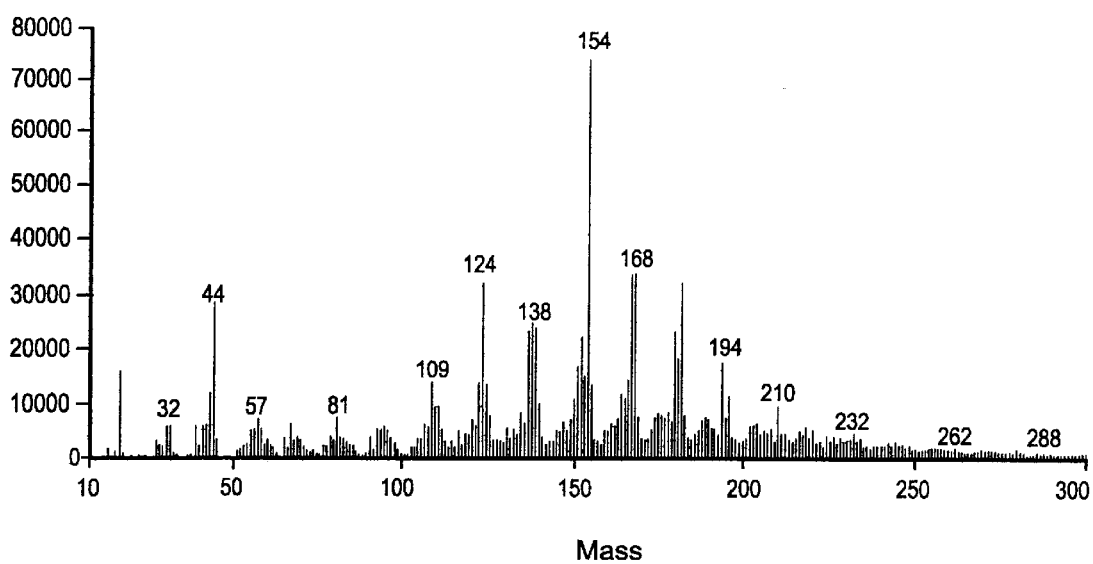

In the same manner as in Example I(b), a second identical 20 sample of the crude lignin of Example XI(a) was placed into a single stage quench reactor along with 39% by weight potassium hydroxide. The reactor was heated to 600° C. at atmospheric pressure for 1–3 minutes, and the vapors produced therefrom were analyzed using the mass spectrometer. FIG. 7(b) illustrates the overall increased yield of low molecular weight compounds.

EXAMPLE XII(a)

Figure 8A:
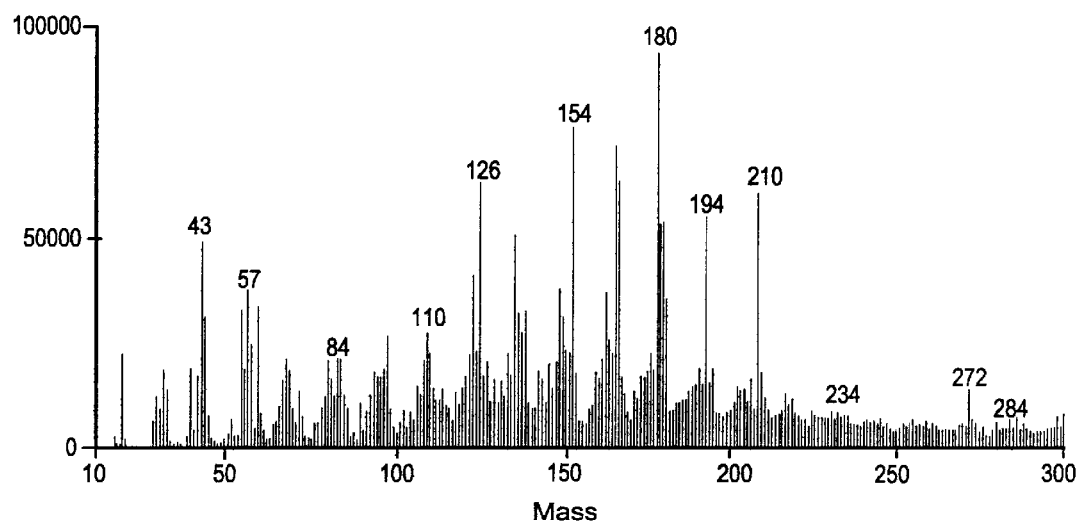
FIGS. 8(a) and (b) are graphs showing comparative pyrolysis data of a second crude lignin whose source is an SSF residue.

In the same manner as in Example XI(a), a sample of SSF residue (crude lignin) from ethanol production was placed in a single stage quench reactor. The crude lignin residue was from black locust wood. The reactor was heated to 600° C. at atmospheric pressure for 1–3 minutes, and the vapors produced therefrom were analyzed using the mass spectrometer as shown in FIG. 8(a).

EXAMPLE XII(b)

Figure 8B:
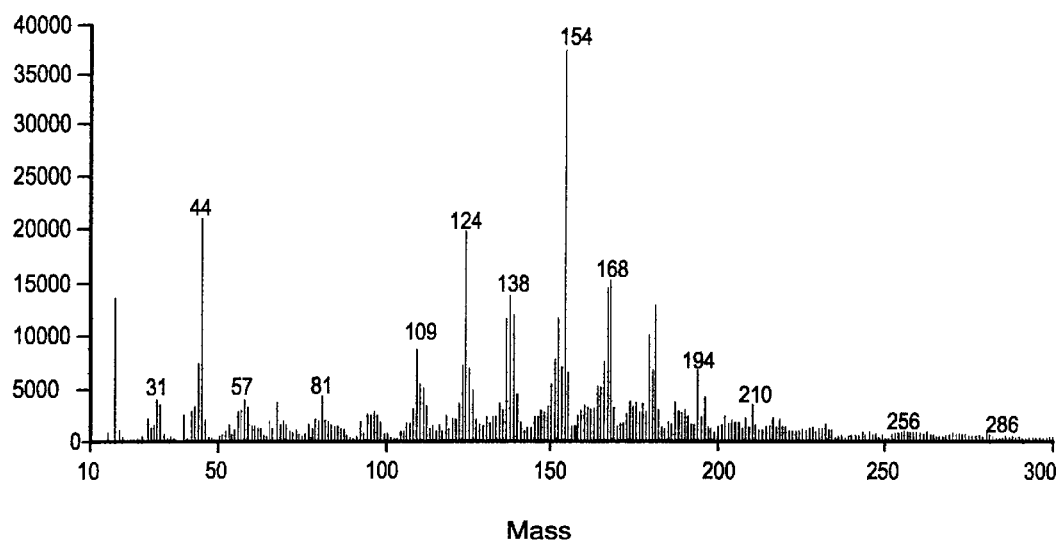

In the same manner as in Example XI(b), a second identical sample of the crude lignin of Example XII(a) was placed into a single stage quench reactor along with 40% by weight potassium hydroxide. The reactor was heated to 600° C. at atmospheric pressure for 1–3 minutes, and the vapors produced therefrom were analyzed using the mass spectrometer. FIG. 8(b) illustrates the overall increased yield of low molecular weight compounds.

It is to be recognized that the relatively high respective amounts of potassium hydroxide required in Examples XI(b) and XII(b) are caused by potassium hydroxide reaction with inorganic salts used in the pretreatment of feedstocks. Thus, most of the potassium hydroxide added to the SSF residue reacted with these salts, and only excess potassium hydroxide reacted with the actual SSF residue to produce the low molecular weight phenolics. When the SSF residue was washed with water prior to treatment with potassium hydroxide, the amount of potassium hydroxide required fell to 6%–10% instead of 39%–40% as required in Examples XI(b) and XII(b). Because of the reactivity of potassium hydroxide, raw biomass could not be used as a starting material because both the cellulose and hemicellulose there present would react with the potassium hydroxide to yield a mixture of products which would be only partially phenolics. Thus, raw biomass must be pretreated to remove the carbohydrate fraction as in an SSF residue production exemplified in Examples XI and XII.

The yield of low molecular weight phenolics from the SSF residue were in the 50%–60% range. The char yields from the pyrolysis of sucrolin and SSF residue varied from 30%–50%(wt).

As is evident from the results here reported, the process of pyrolyzing a lignin in the presence of a strong base such as potassium hydroxide greatly increases the yield of valuable, low molecular weight phenolic compounds. These phenolic compounds can be readily incorporated as precursors in the production of subsequently formulated products. Even the char waste product produced during pyrolysis is a potentially valuable commodity in the production of carbon molecular sieves.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:

1. A process for the production of a phenolic compound substantially in liquid form having a molecular weight from about 100 to (300) less than 168, which molecular weight was determined using multivariate techniques, from a single lignin or a mixture of different lignins, the process comprising:
   a) pyrolyzing the lignin mixture of lignins in the presence of from about 0.1% to about 5% by weight of a strong base at a temperature of from about 400° C. to about 600° C. for a time period of from about one minute to about three minutes recover a yield of at least 15% low molecular weight phenolic compounds from the single lignin or the mixture of different lignins.

2. A process for the production of a phenolic compound substantially in liquid form having a molecular weight from about 100 to (300) less than 168, which molecular weight was determined using multivariate techniques, from a single lignin or a mixture of different lignins, the process comprising:
   a. pyrolyzing the lignin or mixture of lignins in the presence of from about 0.1% to about 5% by weight of a strong base at a temperature of from about 400° C. to about 600° C. to recover a yield of at least 15% low molecular weight phenolic compounds from the single lignin or the mixture of different lignins, and wherein the time period is from about one to about five minutes.

3. A process as claimed in claim 2 wherein the process is performed at atmospheric pressure.

4. A process as claimed in claim 3 wherein the base is potassium hydroxide.

5. A process as claimed in claim 4 wherein lignins are chosen from the group consisting of mixed hardwood organosolv lignin, steam exploded yellow poplar lignin, steam exploded aspen lignin, kraft lignin, bagasse lignin, fungi treated corn stover, and mixtures thereof.

6. A process as claimed in claim 5 wherein the temperature is about 600° C.

7. A process as claimed in claim 6 wherein the phenolic compound produced is chosen from the group consisting of methoxyphenols, non-methoxylated phenols, and mixtures thereof.

8. A process as claimed in claim 7 wherein from about 0.01% to about 0.9% by weight potassium ferricyanide is present.

9. A process as claimed in claim 1 wherein the phenolic compound produced is chosen from the group consisting of methoxyphenols, non-methoxylated phenols, and mixtures thereof.

10. A process as claimed in claim 1 wherein from about 0.01% to about 0.9% by weight potassium ferricyanide is present.

11. A process as claimed in claim 1, wherein the lignin or mixture of lignins is sucrolin.

12. A process as claimed in claim 1, wherein the lignin or mixture of lignins are present in a simultaneous saccharification and fermentation residue.

13. A process as claimed in claim 1, wherein the yield is 50%–60% low molecular weight compounds from the lignin or lignins.

14. A process as claimed in claim 13, wherein the pyrolysis of the lignin or lignins produces 30%–50% (wt) char.

15. A process as claimed in claim 12, wherein the yield is 50%-16% low molecular weight compounds are from the lignin or lignins.

16. A process as claimed in claim 14, wherein the pyrolysis of the lignin or lignins produces 30%–50% (wt) char.

17. A process for the production of a phenolic compound substantially in the form of a liquid having a molecular weight determined by multivariate techniques from about 100 to less than 168 from a single lignin or a mixture of different lignins, the process comprising:
   a) pyrolyzing the lignin for a period of from about one to about five minutes at a temperature of from about 400° C. to about 600° C. in the presence of a strong base at a concentration sufficient to recover a yield of at least 15% of the phenolic compound.

18. A process as claimed in claim 17, wherein the process is performed at atmospheric pressure.

19. A process as claimed in claim 18, wherein the base is potassium hydroxide.

20. A process as claimed in claim 19, wherein lignins are chosen from the group consisting of mixed hardwood organosolv lignin, steam exploded yellow poplar lignin, steam exploded aspen lignin, kraft lignin, bagasse lignin, fungi treated corn stover, and mixtures thereof.

21. A process as claimed in claim 20, wherein the temperature is about 600° C.

22. A process as claimed in claim 21, wherein the phenolic compound produced is chosen from the group consisting of methoxyphenols non-methoxylated phenols and mixtures thereof.

23. A process as claimed in claim 23, wherein from about 0.01% to about 0.9% by weight potassium ferricyanide is present.

24. A process as claimed in claim 17, wherein the phenolic compound produced is chosen from the group consisting of methoxyphenols, non-methoxylated phenols, and mixtures thereof.

25. A process as claimed in claim 24, wherein from about 0.01 to about 0.9% by weight potassium ferricyanide is present.

26. A process as claimed in claim 25, wherein the lignin or mixture of lignins is sucrolin.

27. A process as claimed in claim 26, wherein the lignin or mixture of lignins are present in a simultaneous and fermentation residue.

28. A process as claimed in claim 27, wherein the yield is a 50%–60% low molecular weight compounds from lignin or lignins.

29. A process as claimed in claim 28, wherein the pyrolysis of the lignin or lignins produces 30%–50% (wt) char.

* * * * *